(12) United States Patent
Gebauer et al.

(10) Patent No.: US 9,958,421 B2
(45) Date of Patent: May 1, 2018

(54) METHOD FOR DRY PACKING CHROMATOGRAPHY COLUMNS

(75) Inventors: Klaus Gebauer, Uppsala (SE); Elisabeth Hallgren, Uppsala (SE); Raf Lemmens, Uppsala (SE); Ola Lind, Uppsala (SE); Bjorn Lundgren, Uppsala (SE); Jamil Shanagar, Uppsala (SE); Kajsa Stridsberg-Friden, Uppsala (SE); Helena Widegren, Uppsala (SE)

(73) Assignee: GE Healthcare BioProcess R&D AB, Uppsala (SE)

( * ) Notice: Subject to any disclaimer, the term of this patent is extended or adjusted under 35 U.S.C. 154(b) by 474 days.

(21) Appl. No.: 13/518,029

(22) PCT Filed: Dec. 20, 2010

(86) PCT No.: PCT/SE2010/051424
§ 371 (c)(1),
(2), (4) Date: Jun. 21, 2012

(87) PCT Pub. No.: WO2011/078772
PCT Pub. Date: Jun. 30, 2011

(65) Prior Publication Data
US 2012/0267299 A1    Oct. 25, 2012

(30) Foreign Application Priority Data
Dec. 22, 2009  (SE) ........................... 0951003

(51) Int. Cl.
*G01N 30/56*   (2006.01)
*B01D 15/20*   (2006.01)
(Continued)

(52) U.S. Cl.
CPC .......... *G01N 30/56* (2013.01); *B01D 15/206* (2013.01); *B01D 15/32* (2013.01); *B01D 15/361* (2013.01);
(Continued)

(58) Field of Classification Search
None
See application file for complete search history.

(56) References Cited

U.S. PATENT DOCUMENTS 4,170,454 A     10/1979 Meriadec et al.
4,175,037 A  *  11/1979 Benney et al. ................. 141/12
(Continued)

FOREIGN PATENT DOCUMENTS

CA    1 119 102    3/1982
GB    767 469      2/1957
(Continued)

OTHER PUBLICATIONS

Q Sepharose Fast Flow. GE Healthcare Life Sciences. Retrieved Feb. 2, 2015 from <http://www.gelifesciences.com/ . . . >.*
(Continued)

*Primary Examiner* — Katherine Zalasky
*Assistant Examiner* — Kara Graber
(74) *Attorney, Agent, or Firm* — Wood IP LLC (57) ABSTRACT

The invention provides a packing method for high efficiency chromatography columns starting from dry swellable particles, as well as columns packed by the method and the use of the columns in separation of biomolecules. In the packing method, an amount of dry swellable particles sufficient to give a swollen volume in a liquid of about 105-120% of the column chamber volume is transferred to the column, the column is closed and the liquid is provided to the column.

8 Claims, 7 Drawing Sheets (51) Int. Cl.
*G01N 30/28* (2006.01)
*B01J 20/28* (2006.01)
*B01D 15/32* (2006.01)
*B01J 20/22* (2006.01)
*B01D 15/36* (2006.01)
*B01J 20/281* (2006.01)
*B01J 20/30* (2006.01)
*B01D 15/38* (2006.01)
*B01J 20/285* (2006.01)

(52) U.S. Cl.
CPC .......... *B01D 15/3804* (2013.01); *B01J 20/22* (2013.01); *B01J 20/28* (2013.01); *B01J 20/285* (2013.01); *B01J 20/28011* (2013.01); *B01J 20/28016* (2013.01); *B01J 20/3092* (2013.01); *G01N 30/28* (2013.01); *G01N 30/482* (2013.01)

(56) References Cited

U.S. PATENT DOCUMENTS

| | | | |
|---|---|---|---|
| 4,259,186 A | 3/1981 | Boeing et al. | |
| 4,353,801 A | 10/1982 | Mukoyama et al. | |
| 4,366,060 A | 12/1982 | Leiser et al. | |
| 2003/0146159 A1 | 8/2003 | Guiochon | |
| 2007/0193933 A1 | 8/2007 | Vidalinc | |
| 2007/0259968 A1* | 11/2007 | Menzler | C08F 2/18 514/772.4 |
| 2008/0154031 A1* | 6/2008 | Berg et al. | 536/123.1 |
| 2008/0217248 A1 | 9/2008 | Gebauer | |

FOREIGN PATENT DOCUMENTS

| | | |
|---|---|---|
| JP | 03-197862 | 8/1991 |
| JP | 2009-250862 | 10/2009 |
| WO | WO 1993/003841 | 3/1993 |
| WO | WO 2008/009412 | 1/2008 |

OTHER PUBLICATIONS

Sepharose 4B. GE Healthcare Life Siceinces. Retrieved Feb. 2, 2015 from <http://www.gelifescience.com/ . . . >.*
Institute of Molecular Development. Molecular Techniques and Methods. Protein Purification by Ion Exchange Chromatography. 2001. Retrieved Feb. 5, 2015 from <http://www.molecularinfo.com . . . >.*
Dolan, J. Why Do Peaks Tail? LC Troubleshooting. Sep. 2003.*
Snyder, L.R., Kirkland, J.J. Introduction to Modern Liquid Chromatography. Second Edition. John Wiley & Sons, Inc. 1997.*
Amberlite 200C Na. Industrial Grade Strong Acid Cation Exchanger. Rohm and Haas. Jan. 2008.*
EP Search Report Dated Jan. 8, 2014 Issued on Corresponding EP Application No. 10839893.4.
CN Search Report Dated Dec. 4, 2013 Issued on Corresponding CN Application No. 201080058776.9.

* cited by examiner

METHOD FOR DRY PACKING CHROMATOGRAPHY COLUMNS

CROSS-REFERENCE TO RELATED APPLICATIONS

This application is a filing under 35 U.S.C. 371 of international application number PCT/SE2010/051424, filed Dec. 20, 2010, published on Jun. 30, 2011 as WO 2011/078772, which claims priority to application number 0951003-3 filed in Sweden on Dec. 22, 2009.

TECHNICAL FIELD OF THE INVENTION

The present invention relates to packed bed columns useful for liquid chromatography separation of biomolecules, to a method of packing such columns and to methods of separating biomolecules with the columns.

BACKGROUND OF THE INVENTION

Columns used in liquid chromatography typically comprise a tubular body enclosing a packed bed of porous chromatography medium through which a carrier liquid flows, with separation taking place by partitioning between the carrier liquid and solid phase of the porous medium.

Prior to any separation process, the bed has to be prepared by starting from the particulate medium that is to be introduced into the column. The process of bed formation is called 'the packing procedure' and a correctly packed bed is a critical factor influencing the performance of a column containing a packed bed. Typically, the packed bed is prepared by slurry packing, i.e. consolidating a suspension of discrete particles in liquid, known as slurry that is pumped, poured, or sucked into the column. Once the predetermined volume of slurry has been delivered into the column it needs to be further consolidated and compressed by moving a movable adapter down the longitudinal axis of the column towards the bottom of the column, normally at a constant speed. The excess liquid during this procedure is expelled at the column outlet, while the media particles are retained by means of a filter material, a so-called 'bed support', with pores too small to allow the media particles to pass though. The packing process is complete once the packed bed has been compressed by the optimum degree of compression. Another approach for column slurry packing is the flow packing method, where compression of the porous structure is primarily achieved by applying a high flow rate over the column, hereby forming a porous structure starting at the outlet bed support. The resulting drag force on the particles in the porous structure causes eventually a pressure drop and a compression of the bed. The compressed bed is finally confined by bringing the adapter into position.

The efficiency of subsequent chromatographic separation relies strongly on 1) the liquid distribution and collection system at the fluid inlet and outlet of the packed bed, 2) the special orientation (also know as the packing geometry) of the media particles in the packed bed, and 3) the compression of the packed bed. If the compression of the packed bed is too low then chromatographic separations performed on that bed suffer from "tailing" and, generally, such insufficiently compressed beds are unstable. If the compression of the packed bed is too high then chromatographic separations performed by the bed suffer from "leading" and such over-compressed beds can affect throughput and binding capacity, and, in general, give much higher operating pressures. If the compression is optimum, then the separation peaks formed during use exhibit much less leading or tailing and are substantially symmetrical. The optimum degree of compression is also crucial for achieving good long-term stability of the porous structure, hereby securing optimal performance throughout a number of process cycles. The optimum degree of compression required for a column is determined experimentally for each column size (width or diameter), bed height, and media type.

An alternative packing method is called "dry packing", where the column is filled with dry particles of the porous medium and liquid is introduced in the column afterwards. This has advantages in prepacked columns that can be delivered dry to the customer without having to add any preservatives to the packing liquid and minimizing weight during transport. Dry packing is typically used for silica media aimed at separation of small molecules, as described e.g. by G Guiochon J Chromatogr A 704 (1995) 247-268, although fairly poor column efficiencies are obtained. For swellable chromatography media, such as dextran or agarose-based media commonly used in separation of biomolecules, dry packing has however been avoided due to a perception that the swelling of the particles will cause poor performance of the packed bed. U.S. Pat. No. 4,353,801 mentions dry packing of solvent-swellable styrene-divinylbenzene particles as being inferior to wet packing.

SUMMARY OF THE INVENTION

One aspect of the present invention is to provide a packing method for a high efficiency chromatography column starting from dry swellable particles. This is achieved with a method comprising the steps of a) transferring to a column chamber 2 in a chromatography column 1 an amount of said dry swellable particles 5 sufficient to give a swollen volume Vs in a liquid of about 105-120% of the column chamber volume, b) closing the column and c) providing said liquid to the column. In other words, the method comprises metering out (e.g. by weighing) an aliquot of dry swellable particles 5, providing said aliquot to a column chamber 2 in a chromatography column 1, closing the column chamber and supplying a liquid to the column chamber, wherein the swollen volume Vs of said aliquot is about 105-120% of the column chamber volume.

A specific aspect of the invention is a storage stable prepacked column that is easily shipped to the user and equilibrated by the user. This is achieved by a column comprising dry swellable particles, wherein the amount of particles is sufficient to give a swollen volume Vs in an aqueous liquid of about 105-120% of the column chamber volume.

One or more of the aspects above may be achieved by the present invention as defined by the appended claims. Additional aspects, details and advantages of the invention will appear from the detailed description and claims that follow.

DEFINITIONS

The term "swellable particles" means herein particles that increase in size upon immersion in a liquid. This can be observed as a sediment volume in the liquid which is significantly larger than the bulk volume of the same amount of dry particles.

The term "swollen volume" (Vs) means herein the sediment volume of an aliquot of particles suspended and equilibrated in a liquid. The sediment volume can be measured by suspending the aliquot of particles, equilibrating for up to 24 h, resuspending the particles if needed, letting the particles sediment and measuring the sediment volume in a graded vessel (e.g. a measuring cylinder).

The term "liquid uptake" (Vs/md) means herein the ratio between the swollen volume Vs of an aliquot of particles as defined above and the dry weight and of the particle aliquot before immersion in the liquid.

DETAILED DESCRIPTION OF EMBODIMENTS

Figure 1:
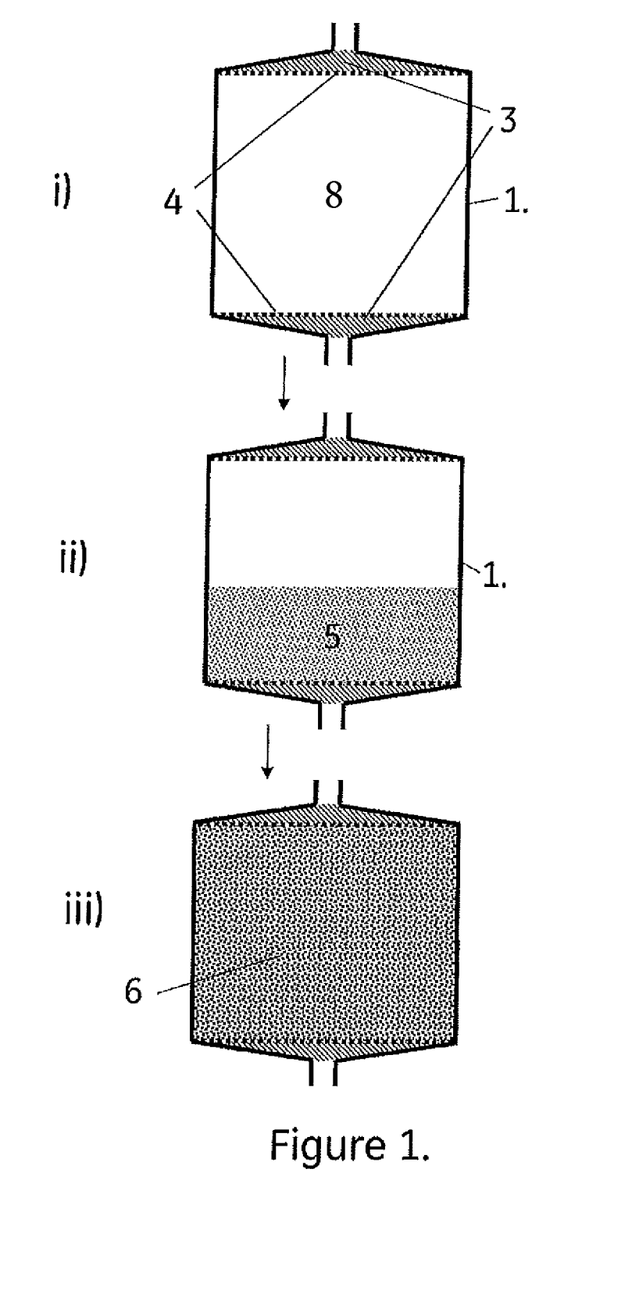
FIG. 1 shows a schematic drawing of a column and the method of packing it with dry swellable particles.
Figure 4:
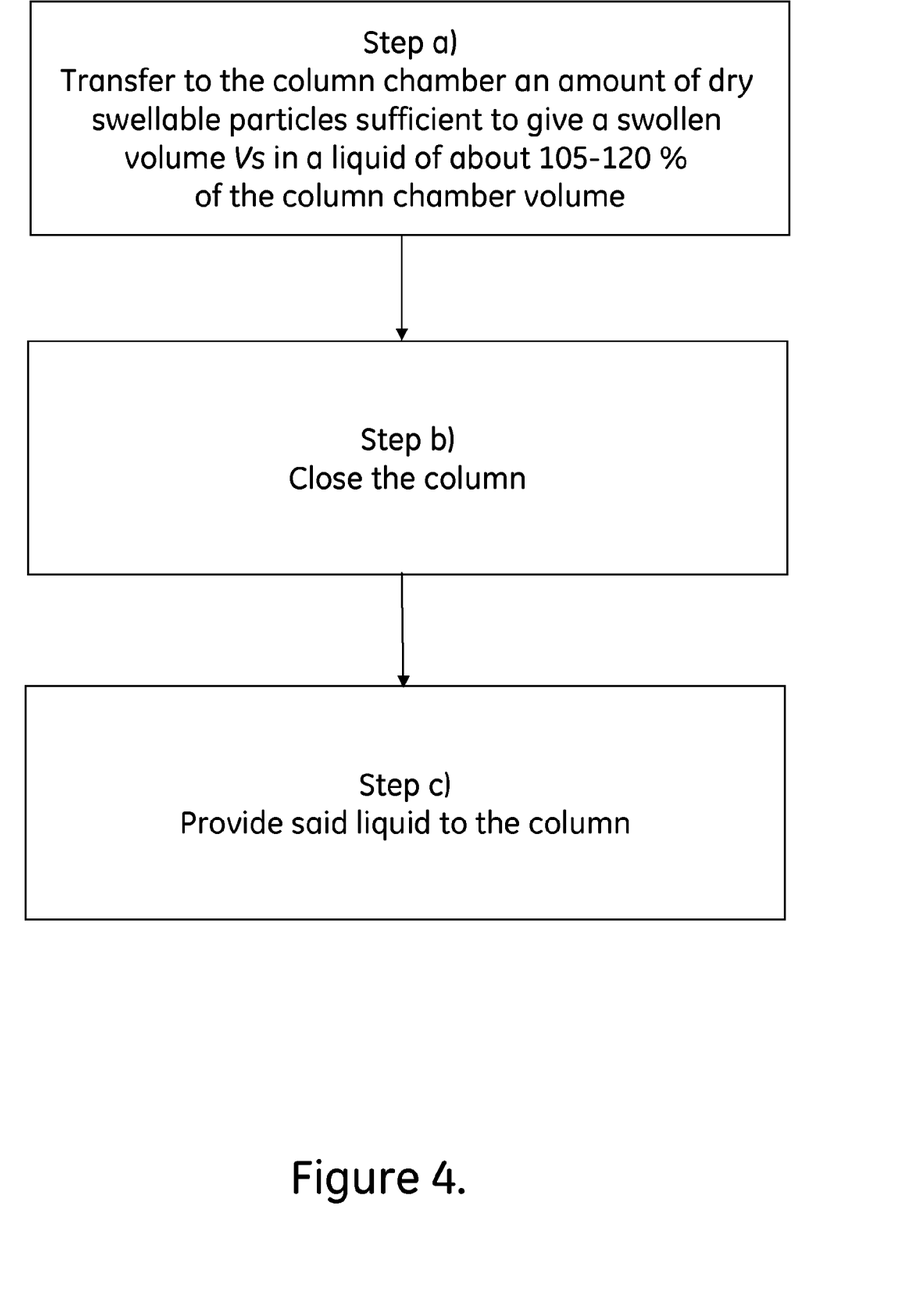
FIG. 4 shows a flow diagram of the packing method.

In one embodiment of the invention, illustrated in FIGS. 1 and 4, an amount of dry swellable particles 5 is transferred to a column chamber 2 in a chromatography column 1, wherein the amount of particles is sufficient to give a swollen volume Vs in a liquid of about 105-120% of the column chamber volume, the column is closed and the liquid is supplied to the column chamber. Since the swollen volume is higher than the column chamber volume, the particle bed will be compressed to a corresponding degree (the compression factor CF for a packed column is usually defined as Vs/Vcol, where Vcol is the column chamber volume), which provides for a high column efficiency and low peak asymmetry. The column efficiency can be expressed as the reduced plate height h, which is the plate height divided by the average diameter of the particles. The plate height is measured by methods well known in the art. The peak asymmetry can be expressed as the asymmetry factor As, which is the ratio between the distance from the back slope of a peak to the center of the peak and the distance from the front slope to the peak center (all measured at 10% of the peak height). Both the plate height and the asymmetry factor are suitably measured for small molecule non-retained species. The column may be designed for axial or radial flow and it may comprise fluid distributors 3. The inlet and outlet of the column chamber may be delimitated by porous screens 4 to retain the particles and let liquids pass. The porous screens may be prepared from woven meshes, sintered frits or any other type of porous material.

Figure 5:
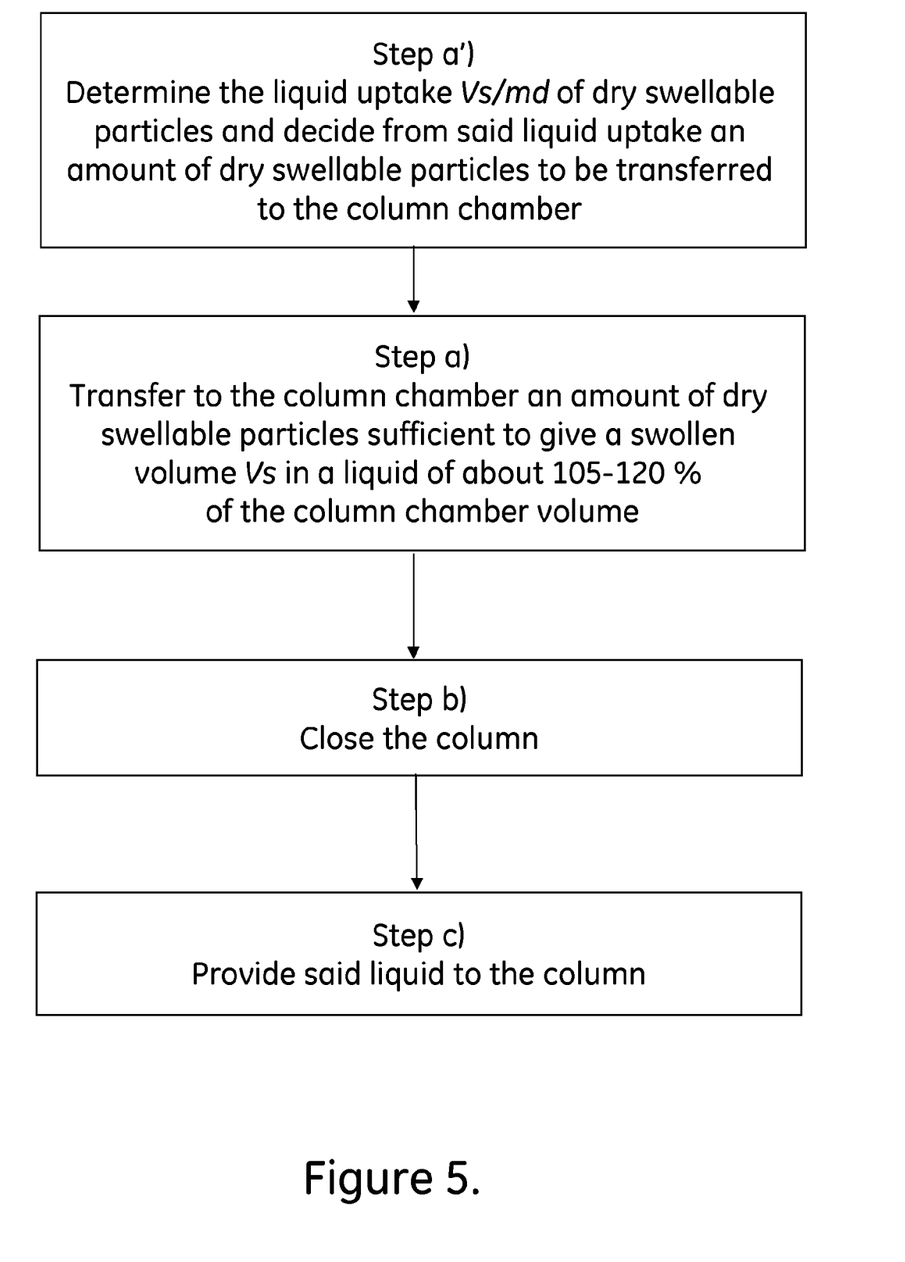
FIG. 5 shows a flow diagram of an embodiment where the liquid uptake of the dry swellable particles is determined.

In a further embodiment, depicted in FIG. 5, an initial step in the method is to determine the liquid uptake Vs/md of the dry swellable particles and to decide from said liquid uptake the amount of dry swellable particles to be transferred to the column chamber. The liquid uptake can be determined from a separate sample aliquot of the particles, using established methods for taking representative samples. The sample is weighed dry (i.e. in equilibrium with the ambient atmosphere) and is then suspended in a test liquid. The test liquid can be the same liquid to be used in the packing and operation of the column or a liquid of similar composition; typically an aqueous buffer or salt solution of similar ionic strength/conductivity and pH. The particles in the test liquid are left to equilibrate, typically for about one hour and in any case not more than 24 hours. The particles are resuspended and left to sediment. The sediment volume is measured e.g. in a measuring cylinder. The liquid uptake is then calculated as the ratio Vs/md between the sediment volume Vs and the weight md of the dry particle sample. An advantage of initially measuring the liquid uptake is that the swollen volume of the particles in the column can be predicted, resulting in better control of the compression and column efficiency. In a specific embodiment the liquid uptake is determined with less than 5% coefficient of variation or even less than 2% coefficient of variation to allow for high precision in the control of the column performance.

In an alternative embodiment, the liquid uptake is determined on basis of dry particle volume instead of using the weight of the dry particles as reference. Equally, preparation of aliquots to be filled into at least one column of a given specific column may be conducted on basis of dry particle volume instead of dry particle mass.

In certain embodiments the dry swellable particles in the column chamber can be manipulated to allow for a more even spatial distribution before the providing of liquid to the column. In one embodiment, illustrated in FIG. 6, the column is subjected to vibration before the providing of liquid and in another embodiment gas (e.g. air) is injected from the bottom end of the column before the providing of liquid. Both of these actions can cause at least partial fluidisation of the dry particles, leading to a more even distribution of the particles over the horizontal bottom surface of the column chamber. An advantage of this is that a more even spatial distribution of the swollen particles after application of the liquid may be achieved. The vibration or gas injection may be performed at any stage after the transfer of the dry swellable particles to the column chamber or a flexible container. In one embodiment an inert gas may be injected into the column to provide protection against oxidative degradation reactions during storage.

In one embodiment the liquid is provided to the column in the upflow direction. The liquid will then rise evenly in a vertical direction from the bottom inlet through the dry particle bed, resulting in a more even particle distribution than if the liquid is pouring down from the top of the column once the particles have been swollen by the liquid, the column may then be operated in any direction (upflow, downflow, tilted etc.) In a specific embodiment the rate of liquid addition to the dry swellable particles does not exceed the rate of capillary suction by the particles. The rate of capillary suction can be determined e.g. by placing a column with dry swellable particles in a trough containing liquid up to the lower end of the dry bed and measuring the rate of liquid rising through the bed by optical, gravimetric or other methods. Keeping the rate of liquid addition lower or equal to the rate of capillary suction has the advantage of giving a more homogeneous particle distribution after swelling and hence better column performance. The rate of liquid addition can be expressed as the liquid velocity in the column chamber (the liquid flow rate divided by the internal cross section area of the column chamber). In a specific embodiment the liquid velocity in the column chamber is less than 100 cm/h, such as between 5 and 70 cm/h, during the addition of liquid to the dry particles. In one embodiment the liquid is aqueous and it can then comprise a wetting agent (an additive that decreases the surface tension), such as a lower alcohol, e.g. ethanol, or a surfactant. An advantage of this is that a more uniform distribution of the particles after swelling can be obtained.

Figure 2:
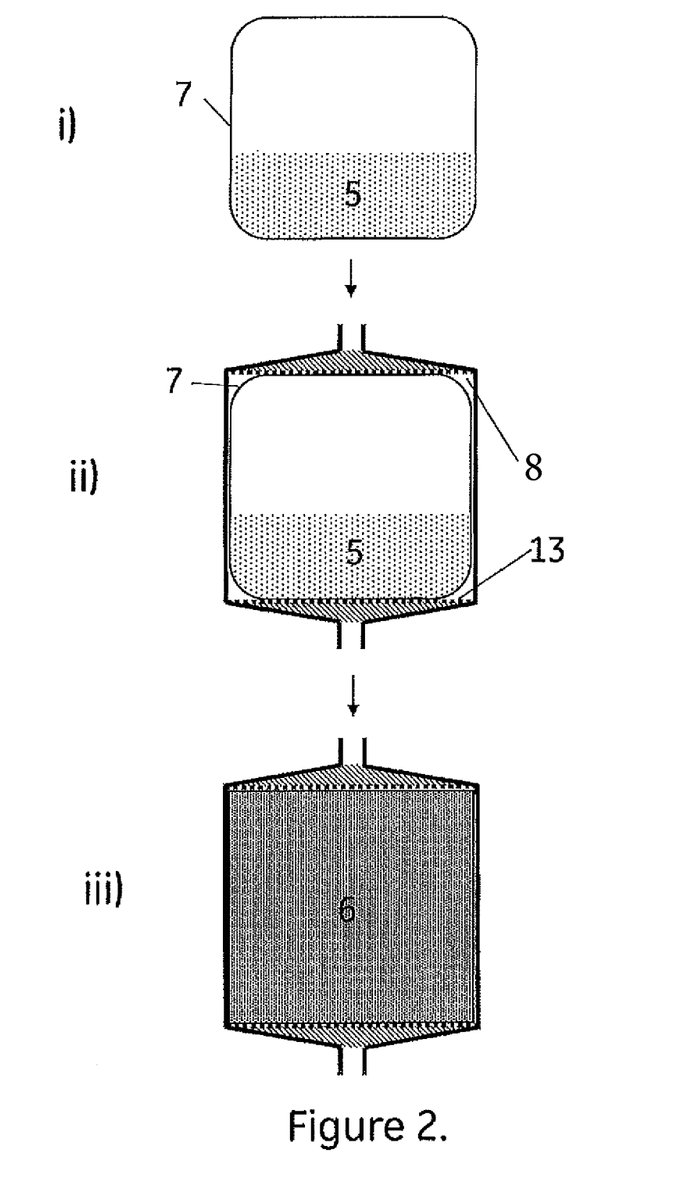
FIG. 2 shows an embodiment with a flexible container inserted in the column chamber.

In one embodiment, depicted in FIG. 2, the step of transferring the swellable dry particles to a column chamber in a chromatography column comprises first transferring the dry swellable particles 5 to a flexible container 7 and then placing the flexible container in the column chamber 2. This has the advantage that the particles can be supplied to the user packaged in an easily transported low-cost flexible container and the user can place the container in the column and apply liquid. The walls of the flexible container can have porous portions to be fitted against the porous top and bottom plates of the column chamber. The flexible container can be e.g. a plastic bag construction or be assembled from molded and/or extruded parts. In one embodiment the flexible container is expanded by the swollen particles to fit the column chamber.

In one embodiment the method comprises, after the transfer of dry swellable particles to the column chamber 8 and before the closure of the column, a step of transferring the column chamber 8 to a rigid housing 11 providing dimensional stability for the column chamber during swelling of the gel and/or operation of the column. In this context, the free-standing column chamber 8 may deflect somewhat during swelling of the gel or due to pressurization during operation of the column. A rigid housing 11 will prevent any such deflection and any associated deterioration of the column performance.

In one embodiment the method comprises before the addition of liquid to the column a step of radiation sterilising the column or the flexible container with the dry swellable particles. This step may be carried out at any stage of the method. The radiation sterilisation can be carried out through gamma or electron beam irradiation.

One embodiment of the invention is a column comprising dry swellable particles, wherein the amount of particles is sufficient to give a swollen volume Vs in an aqueous liquid of about 105-120% of the column chamber volume. In one embodiment this liquid is a 0.1 mol/l solution of sodium chloride (NaCl) in water at 20° C. Such a solution has a conductivity of approx. 10 mS/cm which is in the range of many buffers used in biomolecule/biopharmaceutical separations.

In one embodiment the liquid uptake Vs/md of the dry swellable particles (in 0.1 M aqueous NaCl at 20 C) is between 5 and 25 ml/g, such as between 5 and 15 ml/g. An advantage of this embodiment is a good control of the compression factor and minimised variability in swelling (and column performance) with composition of the liquids applied during operation of the column. In one embodiment the liquid uptake of the dry swellable particles in distilled water is less than 1.5 times the liquid uptake in 0.1M aqueous NaCl. An advantage of this is that the variability in swelling with liquid composition is kept low.

In one embodiment the column volume is fixed. A fixed volume column can be constructed without any moving parts (adaptors etc), which simplifies construction and is advantageous from a cost point of view. In one embodiment the column comprises molded or extruded parts. Molding and extrusion methods such as injection molding, blow molding, rotation molding, compression molding etc are convenient and cost-efficient methods to manufacture column parts from e.g. thermoplastic materials.

In one embodiment the column chamber volume is at least one liter. Columns with more than one liter bed volume are frequently used in industrial biopharmaceutical purification. They are often complicated and expensive steel constructions with moving parts, so solutions allowing use of simple plastic constructions are desirable.

In one embodiment illustrated by FIG. 2, the column 1, comprises a flexible container 7 comprising the dry swellable particles 5. This has the advantage that the particles can be supplied to the user packaged in an easily transported low-cost flexible container and the user can place the container in the column and apply liquid. The flexible container can comprise at least one flexible wall, i.e. a wall that can deflect enough to cause at least 1% volume change of the container when an overpressure of 1 bar is applied to the unsupported container. The walls of the flexible container can have porous portions fitted against the porous top and bottom plates 13 of a column chamber 2. The flexible container can be e.g. a plastic bag construction or be assembled from molded and/or extruded parts. In one embodiment the flexible container is expandable to fit the column chamber upon swelling of the particles. In another embodiment, porous top and bottom plates segments that retain the particles and provide liquid distribution may be incorporated into the flexible container. In this case, the flexible container is a closed system and not in fluid contact with the housing or other parts supporting the flexible container mechanically from the outside.

Figure 3:
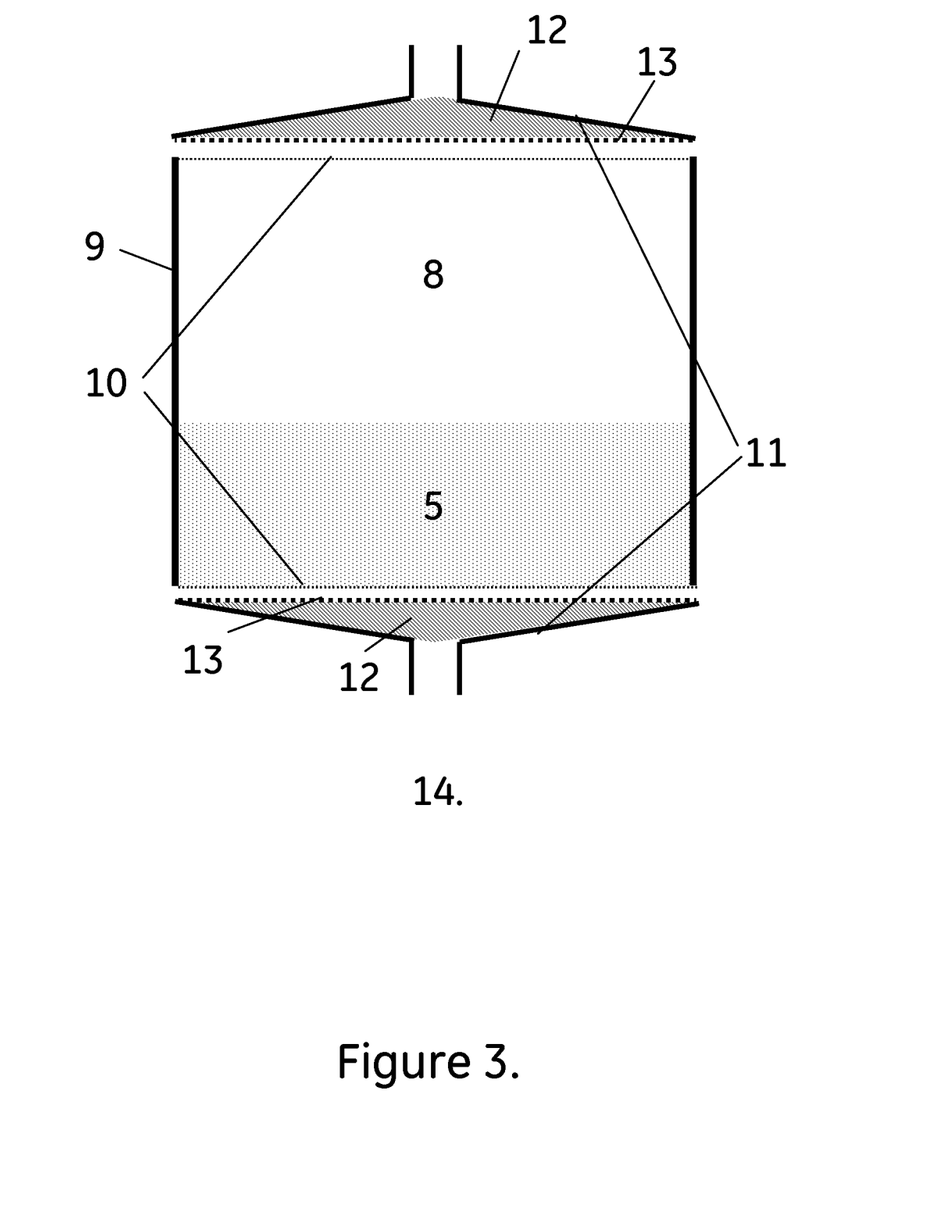
FIG. 3 shows an embodiment with a tubular column chamber mounted in a rigid housing.

In one embodiment illustrated by FIG. 3, the column comprises at least one tubular column chamber 8, with e.g. circular, elliptical or rectangular cross section, with at least one rigid tube wall 9 and at least one flexible endpiece 10. The flexible endpiece can be porous and placed in immediate contact with a porous top or bottom plate 13 in a rigid housing 11. The top and bottom ends of the rigid housing can be held together by a generic clamping structure well known in the art (not shown in FIG. 3).

In one embodiment the dry swellable particles comprise a polysaccharide, such as crosslinked agarose. Crosslinked agarose particles are highly useful for biomolecule and biopharmaceutical purification due to their high throughput and low non-specific adsorption. They are normally supplied in aqueous ethanol solution and an advantage of using dry agarose particles is that no flammable ethanol has to be handled. Drying of agarose particles can be done using e.g. freeze drying, spray drying or vacuum drying.

In embodiment the dry swellable particles comprise charged ligands. Such ligands are predominantly used in ion exchange and multimodal separations, both of which are highly useful in biomolecule and biopharmaceutical separations. Both cation exchangers, anion exchangers and multimodal ion exchangers are contemplated.

In one embodiment the dry swellable particles comprise ligands comprising hydrophobic functionality. Such ligands are used in hydrophobic interaction chromatography and many multimodal separations, both of which are highly useful in biomolecule and biopharmaceutical separations. Examples of ligands and ligand parts with hydrophobic functionality are alkyl and aryl groups.

In one embodiment the dry swellable particles comprise affinity ligands. Such ligands are highly useful for high selectivity separation of biomolecules and biopharmaceuticals. Examples of affinity ligands are protein A, protein G, protein L, lectins, enzyme substrates, lectins, biotin, avidin, antibodies, antibody fragments, antigens etc.

In one embodiment the liquid provided to the column with the dry swellable particles comprises at least one biomolecule, such as a biopharmaceutical. Examples of such liquids include protein solutions and virus suspensions, e.g. feeds to be purified in bioprocessing operations. An advantage of swelling the dry particles directly with a feed is that a separate swelling step can be eliminated and that the swelling in itself can provide a separation and concentration effect for species not penetrating into the swollen structure.

One embodiment of the invention is a column comprising swollen particles, packed according to the previously described embodiments. In a specific embodiment the column has a reduced plate height h less than 15, such as less than 10 for a test species. The test species can be a non-retained small molecule, such as an inorganic salt or acetone. In a further embodiment the asymmetry factor As of the column is less than 3, such as less than 2.5 for a test species selected as above.

One embodiment is at least two columns which are prepared from the same batch of dry swellable particles. In a specific embodiment the columns are connected in parallel. Connection in parallel of columns with the same bed volume, particle type and bed height is a convenient way of increasing the total cross-sectional area and throughput. When columns connected in parallel are used, it is however of great importance that the fluid velocities are identical in the columns to ensure that the same separation is achieved in each column. This puts high demands on the reproducibility of the columns with respect to hydraulic resistance and pressure-flow behavior. With dry swellable particles from the same batch in the columns, it is possible to control the hydraulic resistance and pressure-flow behavior well enough to allow parallel use.

In one embodiment the column comprising swollen particles is used for separation of at least one biomolecule such as a biopharmaceutical. Suitable biomolecules can be proteins, peptides, nucleic acids, carbohydrates, virus particles etc. Suitable biopharmaceuticals can be immunoglobulins (e.g. monoclonal antibodies), immunoglobulin fragments and other constructs, insulin and other therapeutic peptides, erythropoietin, plasma proteins, oligonucleotides, plasmids, vaccines etc. In a specific embodiment the biomolecule or biopharmaceutical is a protein.

In one embodiment the biomolecule or biopharmaceutical binds to the particles and at least one impurity is removed by washing with a washing liquid. The biomolecule or biopharmaceutical may then be eluted from the particles with an elution liquid. This mode is often called bind-elute separation and is particularly useful when the amount of impurities is significant and/or when a very high separation selectivity is required.

In another embodiment at least one impurity binds to the particles and the biomolecule or biopharmaceutical is recovered in the flow-through of the column. This mode is often called flow-through separation and provides a very high throughput, particularly when the amount of impurities is relatively low.

Other features and advantages of the invention will be apparent from the following examples and from the claims.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

DETAILED DESCRIPTION OF THE DRAWINGS

FIG. 1 i) shows a schematic drawing of a column 1 with fluid distributors 3 and a column chamber 2 delimitated by porous screens 4.

FIG. 1 ii) shows the column with dry swellable particles 5 in the column chamber.

FIG. 1 iii) shows the column after application of liquid with the now swollen particles 6 filling the column chamber.

FIG. 2 i) shows a schematic drawing of a flexible container 7 with dry swellable particles 5.

FIG. 2 ii) shows the flexible container 7 placed in the column chamber 2 with porous plates 13.

FIG. 2 iii) shows the column after application of liquid with the now swollen particles 6 filling and expanding the flexible container in the column chamber.

FIG. 3 shows a schematic drawing of a column 14 with dry swellable particles 5 in a tubular column chamber 8 with a rigid tube wall 9, flexible porous endpieces 10 and fitted in a rigid housing 11 with fluid distributors 12 and porous plates 13 in contact with the porous endpieces 10.

FIG. 4. is a flow diagram of an embodiment where step a) comprises transferring dry particles to the column, step b) comprises closing the column and step c) comprises supplying liquid to the column.

FIG. 5. is a flow diagram of an embodiment where step a) is preceded by a step a') comprising determining the liquid uptake of the dry particles and from the liquid uptake deciding the amount of particles to transfer to the column.

Figure 6:
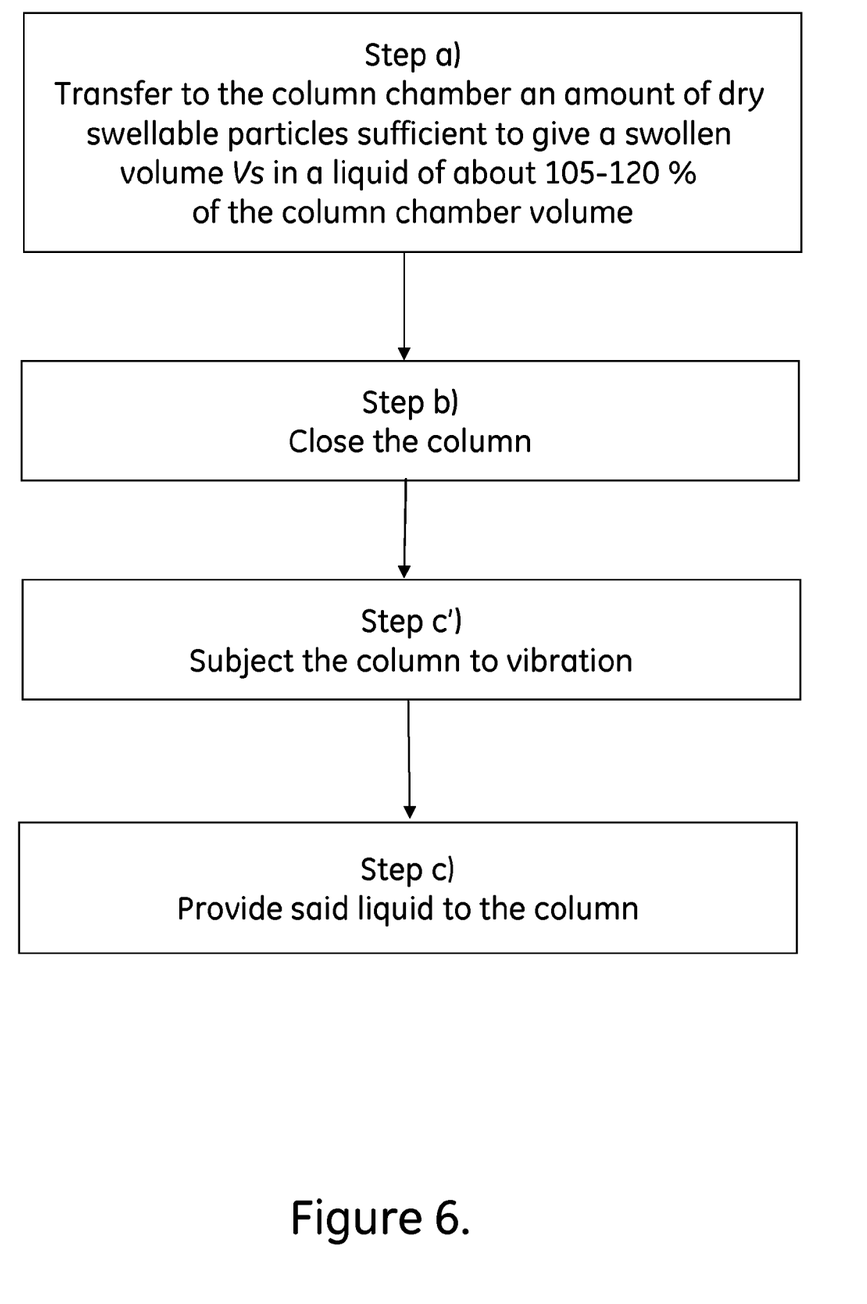
FIG. 6 shows a flow diagram of an embodiment where the column is vibrated before application of liquid.

FIG. 6. is a flow diagram of an embodiment where step c) is preceded by a step c') comprising vibrating the column.

Figure 7:
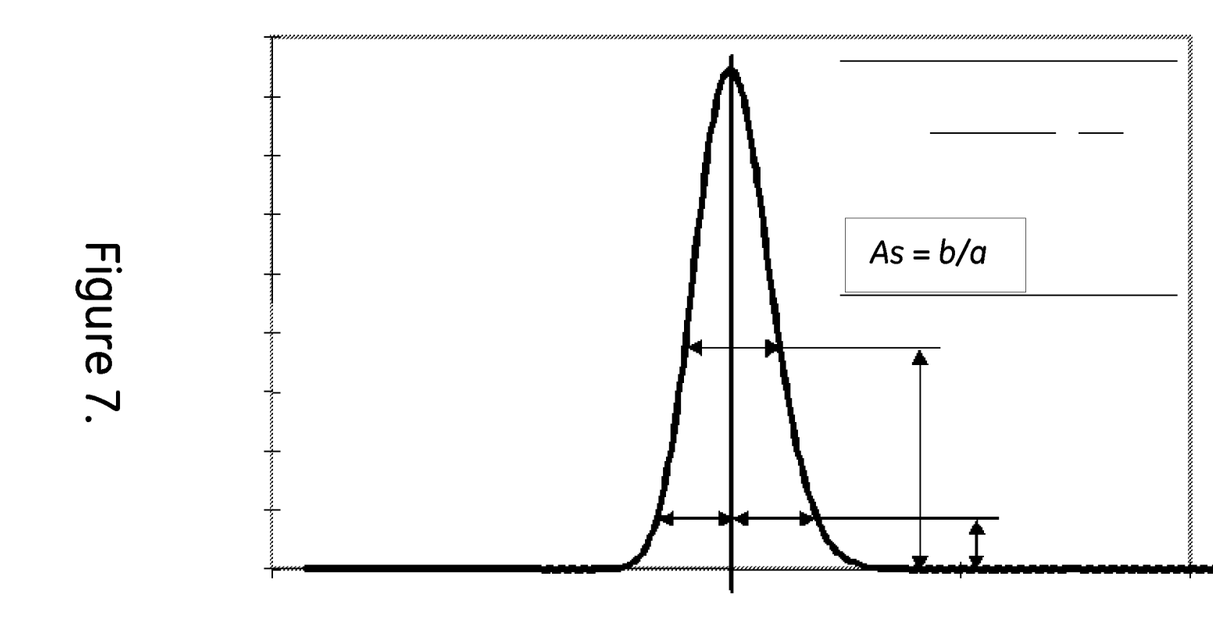
FIG. 7 shows how the column performance is calculated.

FIG. 7 illustrates the calculation of reduced plate height h and asymmetry factor As for a column.

EXAMPLES

Column Efficiency Test

A tracer (acetone 2% v/v in DI water) is applied as tracer with a volume of 1-1.5% of the column volume to analyze the residence time distribution at the column outlet (UV signal @ 280 nm). The residence time distribution should be represented as a single peak, compare FIG. 7. The evaluation is described below.

Column efficiency is typically defined in terms of two parameters:
Peak broadening over the column is described by an equivalent number of theoretical plates (equilibrium stages)
Peak symmetry is described by a peak asymmetry factor $A_s$ The relative peak width is defined as number of (theoretical) plates N, height equivalent of a theoretical plate HETP or preferably as reduced plate height h:

$$N = \frac{\mu_1^2}{\sigma^2} \approx 5.54\left(\frac{V_R}{w_h}\right)^2$$

$$HETP = \frac{L}{N}$$

$$h = \frac{HETP}{d_p} = \frac{L}{d_p}\frac{\sigma^2}{\mu_1^2} \approx \frac{L}{d_p}\frac{1}{5.54}\left(\frac{w_h}{V_R}\right)^2$$

The asymmetry factor $A_s$ describes the deviation from an ideal Gaussian peak shape and calculates from the peak width at 10% of peak height:

$$A_s = b/a$$

| Nomenclature | |
|---|---|
| Plate number | N |
| Mean residence time[1] | $\mu_1$ |
| Variance[1] | $\sigma^2$ |
| Retention time[2] | $t_R$ |
| Retention volume[2] | $V_R$ |
| Peak width at half peak height | $w_h$ |
| Bed height | L |
| Particle diameter | $d_p$ |
| Height equivalent of a theoretical plate | HETP |
| Reduced plate height | $h = HETP/d_p$ |
| Asymmetry factor | $A_s$ |

[1] first and second moments in residence time distribution (RTD) curve derived from integration of tracer signal
[2] retention time (retention volume) corresponding to time (or eluted volume) at maximum peak height

Example 1

The dry swellable particles used were Q Sepharose™ HP (GE Healthcare, Sweden), an anion exchanger with tetramethylammonium group ligands coupled to crosslinked agarose beads of 34 micron average diameter when swollen in water. The Q Sepharose HP particles had been transferred to acetone and then vacuum-dried at room temperature.

129 mg dry particles per ml column chamber volume were transferred to two vertically standing columns of different types: an XK26 column (GE Healthcare, Sweden) having a column chamber of diameter 26 mm, height 30 mm and volume 15.93 ml and an XK50 column (GE Healthcare, Sweden) having a column chamber of diameter 50 mm, height 31 mm and volume 60.87 ml.

A water solution of 20% ethanol was pumped into the bottom inlet of each column with a fluid velocity of 60 cm/h. The pumping was continued until three column chamber volumes had passed the column and three column volumes of distilled water were then pumped through at a fluid velocity of 200 cm/h. The columns were conditioned by 4×3 column chamber volumes of distilled water at 300 cm/h, pumped in alternating upflow and downflow mode.

The performance of the columns was evaluated by the column efficiency test described above. The performance results are given in Table 1.

| Run | N/m | h (—) | As (—) |
|---|---|---|---|
| XK26down002 | 15746 | 1.87 | 2.03 |
| XK26down003 | 15739 | 1.87 | 2.05 |
| XK26up002 | 15969 | 1.84 | 1.96 |
| XK26up003 | 15882 | 1.85 | 2.01 |
| XK50down003 | 10672 | 2.76 | 1.27 |
| XK50down004 | 10818 | 2.72 | 1.31 |
| XK50up003 | 11020 | 2.67 | 1.25 |
| XK50up004 | 10645 | 2.76 | 1.28 |

Example 2

The dry swellable particles used were Capto™ S (GE Healthcare, Sweden), a cation exchanger with sulfonate group ligands coupled to dextran-extended crosslinked agarose beads of 90 micron average diameter when swollen in water. The Capto S particles had been transferred to acetone and then vacuum-dried at room temperature.

3.34 g dry particles were transferred to two a vertically standing XK26 column (GE Healthcare, Sweden) having a column chamber of diameter 26 mm, height 30 mm and volume 15.93 ml A water solution of 20% ethanol was pumped into the bottom inlet of the column with a fluid velocity of 30 cm/h. The pumping was continued until three column chamber volumes had passed the column and 1.5 column volumes of distilled water were then pumped through at a fluid velocity of 100 cm/h.

The performance of the columns was evaluated by the column efficiency test described above. A stability test was also run with 340 cm/h distilled water in upflow mode for 20 h. The performance and stability results are given in Table 2.

| Run | N/m | h (—) | As (—) |
|---|---|---|---|
| Down001 | 3602 | 3.27 | 1.57 |
| Up005 | 4587 | 2.56 | 1.38 |
| Down002 | 4855 | 2.42 | 1.49 |
| Up006 | 5161 | 2.28 | 1.48 |
| Down003 | 4966 | 2.37 | 1.56 |
| Up007 | 5229 | 2.25 | 1.51 |
| Down004 | 5035 | 2.34 | 1.53 |
| Up008 | 5269 | 2.23 | 1.54 |
| Stability test | | | |
| Down001 | 5066 | 2.32 | 1.57 |
| Up001 | 5251 | 2.24 | 1.58 |
| Down002 | 5010 | 2.35 | 1.58 |

All patents, patent publications, and other published references mentioned herein are hereby incorporated by reference in their entireties as if each had been individually and specifically incorporated by reference herein. While preferred illustrative embodiments of the present invention are described, one skilled in the art will appreciate that the present invention can be practiced by other than the described embodiments, which are presented for purposes of illustration only and not by way of limitation. The present invention is limited only by the claims that follow.

The invention claimed is:

1. A method for dry packing a chromatography column with dry swellable particles comprising the steps of:
  a) determining a liquid uptake Vs/md of the dry swellable particles from a separate sample of particles using a weight of the dry swellable particles thereof, and from the liquid uptake Vs/md deciding a weight amount of dry swellable particles to be transferred to a column chamber in the chromatography column, wherein the weight amount of dry swellable particles gives a swollen volume Vs in a liquid of 105-120% of a column chamber volume;
  b) transferring to a flexible container the weight amount of dry swellable particles as determined, based on the liquid uptake, the flexible container being configured to expand to fit the column chamber upon swelling of the dry swellable particles;
  c) transferring the flexible container to the column chamber;
  d) vibrating the chromatography column or injecting gas from the bottom end of the chromatography column; and e) providing, after vibrating the chromatography column or injecting gas, the liquid to the column chamber upon closing the chromatography column.

2. The method of claim 1, wherein the liquid uptake is determined with less than 5% coefficient of variation.

3. The method of claim 1, wherein in step e) the liquid is provided to the chromatography column in an upflow direction.

4. The method of claim 1, wherein in step e) a rate of providing the liquid does not exceed a rate of capillary suction by the dry swellable particles.

5. The method of claim 1, wherein step b) comprises transferring the column chamber to a rigid housing providing dimensional stability for the column chamber during swelling of the dry swellable particles and operation of the chromatography column.

6. The method of claim 1, further comprising before step e) a step of radiation sterilising the chromatography column or the flexible container with the dry swellable particles.

7. The method of claim 1, wherein the liquid provided to the chromatography column with the dry swellable particles includes at least one biomolecule.

8. The method of claim 1, wherein the liquid uptake $V_s/m_d$ of the dry swellable particles is between 5 and 25 ml/g in 0.1M aqueous NaCl at 20° C.

* * * * *